United States Patent [19]

Cook et al.

[11] Patent Number: 5,221,279
[45] Date of Patent: Jun. 22, 1993

[54] ADJUSTABLE TOUCH CONTROL HANDPIECE

[75] Inventors: Kenneth P. Cook, Blue Bell; Robert M. Bross, Ivyland, both of Pa.

[73] Assignee: Surgical Laser Technologies, Inc., Malvern, Pa.

[21] Appl. No.: 596,816

[22] Filed: Oct. 12, 1990

[51] Int. Cl.⁵ ............................................. A61B 17/36
[52] U.S. Cl. ...................................... 606/15; 606/16; 606/167
[58] Field of Search .......................... 606/3, 10–18, 606/167, 20–52; 128/395–398; 604/22, 95, 165

[56] References Cited

U.S. PATENT DOCUMENTS

| | | | |
|---|---|---|---|
| 1,311,494 | 7/1919 | Camp | 606/44 |
| 3,467,098 | 9/1969 | Ayres. | |
| 3,528,424 | 9/1970 | Ayres. | |
| 3,532,095 | 10/1970 | Miller | 606/49 X |
| 3,821,510 | 6/1974 | Muncheryan. | |
| 3,843,865 | 10/1974 | Nath. | |
| 4,313,431 | 2/1982 | Frank. | |
| 4,421,382 | 12/1983 | Doi et al.. | |
| 4,470,414 | 9/1984 | Imaga et al.. | |
| 4,608,980 | 9/1986 | Aihara | 606/16 |
| 4,693,244 | 9/1987 | Daikuzono. | |
| 4,736,743 | 4/1988 | Daikuzono. | |
| 4,770,653 | 9/1988 | Shturman | 604/21 |
| 4,785,805 | 11/1988 | Joffee et al.. | |
| 4,874,371 | 10/1989 | Comben et al. | 604/95 |
| 4,895,145 | 1/1990 | Joffe et al.. | |
| 5,013,312 | 5/1991 | Parins et al. | 606/37 |

FOREIGN PATENT DOCUMENTS 0069351 1/1983 European Pat. Off. .
2826383 12/1979 Fed. Rep. of Germany .
2147209 5/1985 United Kingdom .

*Primary Examiner*—Peter A. Aschenbrenner
*Attorney, Agent, or Firm*—Seidel, Gonda, Lavorgna & Monaco

[57] ABSTRACT

A handpiece for use with laser surgical contact scalpels having a housing or handle portion with a laser enabling button thereon whereby a surgeon may expeditiously cycle the laser between its on and off conditions. The handpiece further including a mechanism for facilitating the longitudinal and rotational adjustment of the surgical scalpel with respect to the handle whereby optical fiber torque may be relieved and whereby the surgical tip may be oriented properly with respect to the laser actuation button. The adjustment mechanism includes torsional and longitudinal travel limits to protect button interconnect wires and means for locking the mechanism thereby to fix the relative positions of the scalpel and handle. The laser enabling button and associated circuitry including a low voltage self-contained power source and, further, optical isolation from the laser source whereby the laser may be cycled by the surgeon through use of the handpiece button without danger of electrical shock to the patient.

17 Claims, 2 Drawing Sheets

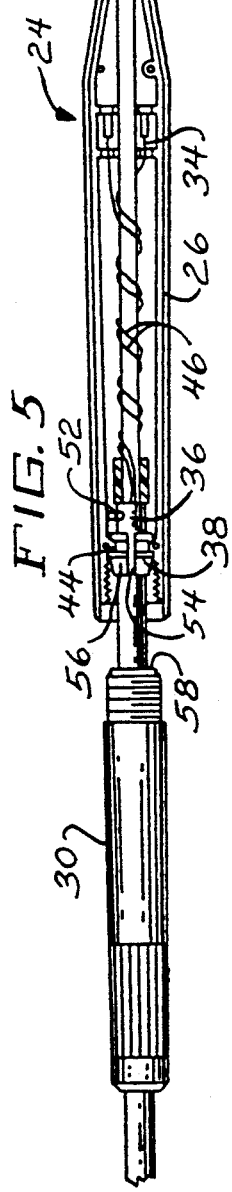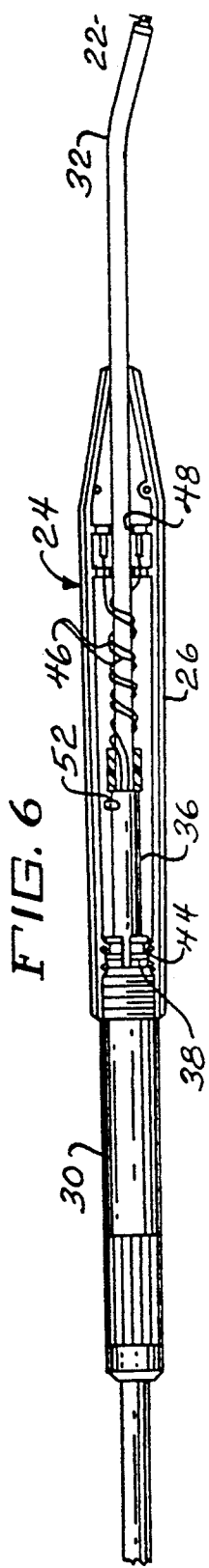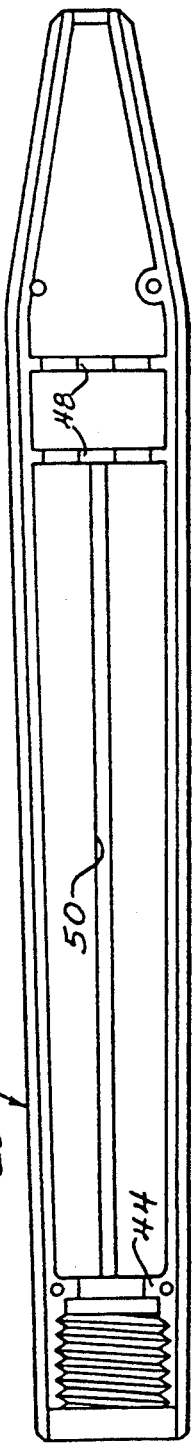
FIG. 5  FIG. 6  FIG. 7

ADJUSTABLE TOUCH CONTROL HANDPIECE

BACKGROUND OF THE INVENTION

The present invention relates to laser surgery apparatus and, more specifically, to a fiber optic delivery system and handpiece for use in contact laser surgery ("contact" and "contact laser" are trademarks of the Applicant, Surgical Laser Technologies, Inc.).

Contact laser surgery has been known for several years. Typically, a source of laser energy, for example Nd:Yag, is coupled to an optical fiber having a sapphire or similar contact member affixed to the distal end thereof. Examples of contact members adapted for several surgical procedures include U.S. Pat. Nos. B1 4,592,353; 4,693,244; and 4,736,743. Examples of a disposable optical fiber delivery suitable for use with the above noted contact members and with the adjustable touch control handpiece of the present invention include U.S. Pat. Nos. 4,785,805 and 4,895,145.

Contact laser surgery has been highly successful in connection with numerous surgical procedures, both internal and external. The present adjustable touch control handpiece is intended principally for external and such other procedures permitting handheld scalpel manipulation.

Conventional handpieces for contact laser surgery typically consist of a tubular member affixed to a handle. A contact member is rigidly retained on the distal end of the tubular member with the optical fiber being routed through the center thereof. In this manner a surgical hand instrument is defined which provides means for physically grasping the relatively small contact member while protecting the fiber optically connected thereto.

It will be appreciated that a laser scalpel has no intrinsic cutting capability, that is, in the absence of an appropriate source of laser energy. (This is in contrast to the steel-edged counterpart with its ever-present knife edge.) In fact, proper operation requires the modulation of the laser energy whereby the laser energy can be interrupted at all times except during the actual incision process.

As a consequence, the surgeon must be provided with an efficacious and instantaneous means for cycling the laser in response to surgical requirements—a means which must at the same time be consistent with the surgeon's substantially full-time attention to the procedure at hand. Foot switches have been used for this purpose.

The present handpiece incorporates an improved means for laser actuation wherein a "touch control" button is positioned on the handpiece generally at the precise location where the handpiece would be grasped during use. In this manner the surgeon may, on-demand and without need for diverting attention from delicate on-going surgical manipulations, call for laser power.

Implementation of the touch control feature presents special problems with respect to the possibility of electrical shock to patients undergoing surgery. Specifically, the touch control feature has been achieved through the use of a totally self-contained touch detection circuit which contains its own source of extremely low voltage energy. In this manner, all possibility for the generation of damaging or lethal electrical currents is eliminated.

This self-contained touch control circuit generates an actuation signal which, in turn, is transmitted to and actuates the laser upon depression of the touch control button. Again, to maintain complete safety against shock hazard, the touch control signal is communicated to the laser utilizing an optical coupler that transmits the signal as "light energy" thereby avoiding direct wire connections.

Another important feature of the present handpiece is its adjustability along and about multiple axes. This feature is particularly advantageous where, as herein described, a touch laser control is provided thereon. As a consequence of this control, the surgeon has only limited flexibility with respect to where and how the handpiece is held—it must be held such that touch button access can be maintained. By contrast, where a footswitch is employed for laser actuation, the surgeon may "choke up" or otherwise grasp the handpiece in any convenient manner.

Thus, as a first degree of adjustability the present handpiece provides for movement along the longitudinal axis whereby the spacing of the surgical laser contact member from the handle portion of the handpiece may be varied as required by the surgeon for his special preferences and for the operative procedure to be performed.

A second or torsional adjustment feature is also provided whereby the angular orientation of the contact member may be varied with respect to the handle with touch control button therein. This adjustment serves two important purposes particularly with respect to the offset style handpiece in which the tubular member is bent and angled outwardly from the instrument longitudinal axis.

First, the surgeon may adjust the relative angular relationship between the contact member and the touch control button thereby positioning the touch button in a more comfortable and easier to access orientation. The second purpose relates to the neutralization of torsional forces which invariably arise by reason of fiber twisting. This twisting results in the presence of an angular bias on the handpiece which is, at a minimum, distracting and uncomfortable. The present invention permits either the manual or automatic cancellation of such torsional forces.

As will become apparent from the detailed description of the preferred embodiment, additional features and advantages of the present handpiece were implemented in combination with and to augment the above-described adjustment and touch control objectives hereof.

For example, as the touch control button must, of functional necessity, be situated on the handle portion of the handpiece, an arrangement to provide for the electrical connection to the touch control switch was required. This arrangement includes a predetermined multiple turn, helically wound fine-wire coil whereby the full longitudinal and rotational movement discussed above can be effected without wire damage or unusual fatigue.

Another feature associated with the above-described adjustment mechanism includes a longitudinally ribbed handle and pin stop arrangement whereby substantially full 360 degree rotational and axial adjustment is realized without damage to the electrical interconnection wiring of the touch control button.

Forming another important aspect of the present system is its adjustment lock in which a particular rotational and longitudinal relationship between the handle and laser scalpel may be set by the surgeon and locked against further movement. This locking mechanism is defined by a slotted collet which coacts with a threaded rear handle member to rigidly grasp and lock the extension tube on which is mounted the scalpel.

These and other features, advantages, and objectives of the present invention will become apparent the figures and specification herein.

BRIEF DESCRIPTION OF THE DRAWINGS

FIG. 5 is a front elevation view of the handle portion of the handpiece of FIG. 1 with portions removed and loosened to reveal internal details thereof;

FIG. 6 is a front elevation view of the handle portion of FIG. 1 with the rear handle member shown in locking engagement with the collet; and, FIG. 7 is a front elevation view of one-half of the main handle housing showing the longitudinal torsion restriction rib therein.

DESCRIPTION OF THE PREFERRED EMBODIMENT

Figure 1:
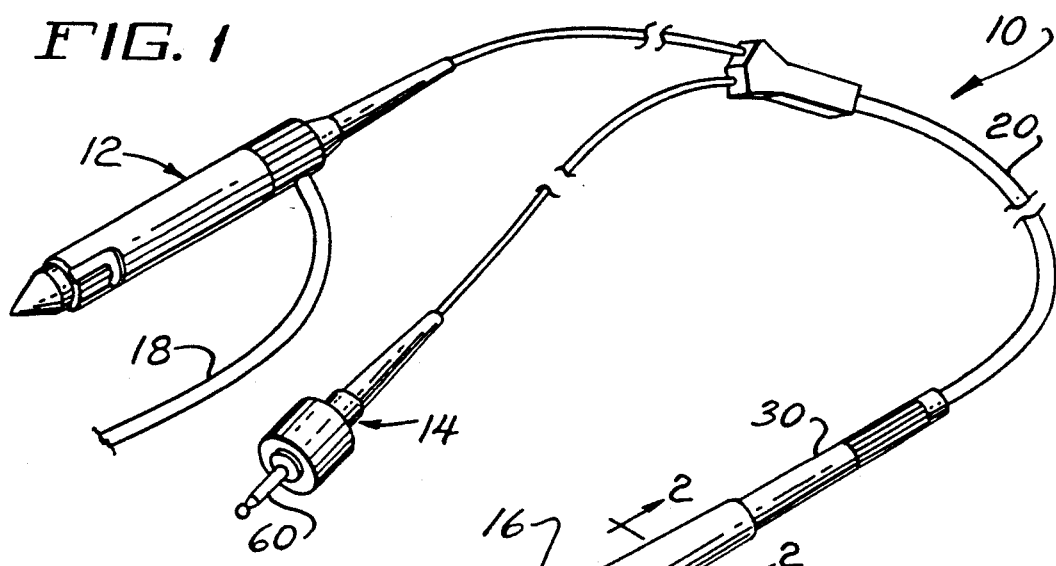
FIG. 1 is a perspective view of the overall handpiece including input connections for the laser energy and touch-control actuation system.

FIG. 1 illustrates the overall touch-control handpiece 10 of the present invention including a connector system 12 for coupling laser energy from the laser source (not shown), a touch-control isolation interface and power source 14, and multi-axes adjustable touch-control handle 16. Connector system 12 further includes an inlet 18 for the admission of cooling fluids and gases. This connector is described in more detail in U.S. Pat. No. 4,895,145 assigned to the present applicant.

A continuous optical fiber positioned within an umbilical 20 serves to transmit the laser energy from connector 12 to the tip end 22 of the touch-control handle. As better shown in FIGS. 5 and 6, screw threads are provided at the tip end and may be used to secure a laser contact scalpel (not shown) thereon. Otherwise, the distal end of the optical fiber may define and serve as the surgical laser output surface.

Referring again to FIG. 1 as well as FIGS. 5 and 6, the touch-control handle 16 is comprised of a main housing 24, which itself is defined by a pair of mating clam-shell members 26 (FIG. 5) and 28 (FIG. 7), a rear housing member 30 screwably received in the fiber inlet end of the housing 24, and an elongate tubular member 32 extending forwardly from the housing onto which, as noted, the operative contact member may be secured. A touch-control push button switch 34 is rigidly positioned forwardly within the housing 24 to permit unrestricted access by the surgeon during handpiece use. As described in more detail below, laser energy is supplied to the operative distal end 22 of the handpiece upon actuation of button 34.

A significant feature of the present invention is the relative adjustability and locking between the housing 24 and the forwardly extending tubular member 32 which adjustability permits the longitudinal elongation of the handpiece as well as the torsional rotation of the tubular member 32. This dual-axis adjustability, in turn, facilitates proper orientation of the operative surgical end 22 with respect to the handle including the ability to relieve any torsional bias on the handle occasioned by twisting of the umbilical 20. In this latter connection it will be understood that a surgeon will generally grasp the housing 24 with the button 34 oriented for convenience of actuation and consequently it will generally be necessary to rotate the member 32 for proper use, particularly if it is of the angled variety as shown in the Figures herein.

FIG. 5 illustrates the present handpiece with the tubular member 32 retracted into the housing 24 thereby shortening the overall instrument, in turn, positioning the operative distal end 22 in relatively close proximity to the housing and surgeon's hand. FIG. 6, by comparison, illustrates the reverse configuration, that is, where the tubular member 32 has been extended with the operative end 22 spaced further from the surgeon's hand.

As best depicted in FIG. 6, the proximal end of tubular member 32 is secured within an inner guide tube 36, for example by epoxy. This inner guide tube extends rearwardly through collet 38 where the guide tube is, in turn, secured to the umbilical 20.

Figure 3:
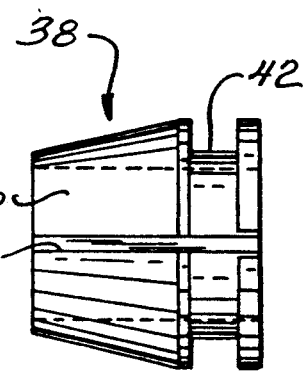
FIG. 3 is a front elevation view of the slotted locking collet of the handpiece of FIG. 1.
Figure 4:
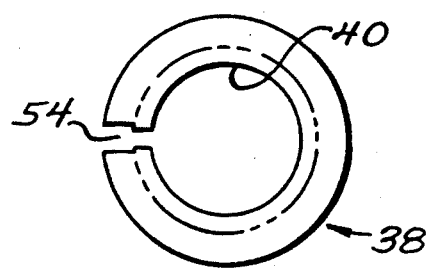
FIG. 4 is a right side elevation view of the slotted locking collet of FIG. 3.

Collet 38, as shown in FIGS. 3 and 4, defines an inside diameter 40 generally equal to the outside diameter of the inner guide tube 36 to thereby receive such tube therein and to lock its axial and torsion as set forth in more detail below. Collet 38 further defines an annular recess 42 to be adapted to be received within a mating annular collar 44 molded into the respect housing clamshells 26 and 28. In this manner, collet 38 is retained within the housing 24 against longitudinal movement while, further, serving as a bearing or housing to permit the axial movement of the inner guide tube 36 therethrough.

The inner guide tube 36 is of sufficient length that it remains within the locking collet 38 through the full range of axial adjustment of tubular member 32. The present handpiece provides for approximately a 1¾" total travel. It will be appreciated that guide tube 36 serves not merely as the passage for the optical fiber, but additionally as the channel through which a pair of wires 46 pass enroute from the actuation switch 34 to the touch-control isolation interface and power source 14. Thus, the optical fiber, including cooling fluid/conduit, and touch-control actuation wires are all contained within umbilical 20.

One or more forward annular collars 48 are integrally formed into each of the clam-shell members to center tubular member 32 while simultaneously serving as bearing surfaces to permit the axial and torsional movement of member 32 within the housing 24.

As clearly seen in FIGS. 5 and 6, the relative axial and torsional movements between the housing 24 (on which push-button switch 34 is mounted) and the umbilical/guide tube combination (through which wires 46 pass) create special problems with respect to the routing and long-term integrity of wires 46. It will be further appreciated that the unrestrained torsional rotation of the umbilical/guide tube within the housing would result in the corresponding twisting and tightening of wires 46, in turn, in the separation of failure of such wires. As a consequence, axial and rotational travel limits have been placed on the relative movement between the umbilical and housing that can be accommodated. Specifically, just under 360 degrees rotation approximately 1¾" axial movement are achieved.

Figure 2:
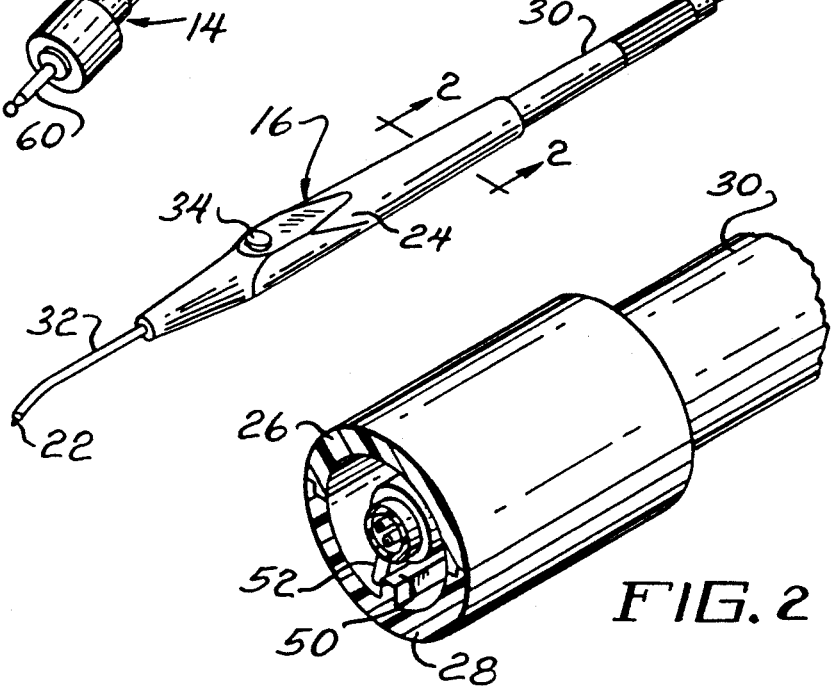
FIG. 2 is a sectional view taken along line 2—2 of FIG. 1.

As best shown in FIGS. 2 and 7, a longitudinal rib 50 is formed within the interior of the housing, for example, in clam-shell housing member 28. This rib extends radially inwardly to a point proximate inner guide tube 36. A pin 52 is positioned generally at the distal end of guide tube 36 and extends radially outwardly therefrom. This pin coacts with the longitudinal rib 50 to block the unrestrained angular movement of the guide tube 36 with respect to the housing. This restriction, as can be seen in FIG. 2, is caused by the interference between the rib and pin wherein the pin cannot rotate past the rib. Pin 52 further serves to limit the axial movement of the guide tube by reason, for example, of an interference between the pin and the collet.

In addition to the above-described restrictions on torsional movement, proper operation and longevity require the appropriate selection wire type/size as well as the special wire dimensioning and contoured routing as set forth hereinafter. More specifically, the exposed wire 46 (i.e. that which extends from the inner guide tube 36 to switch 34) must be of sufficient length to accommodate both the maximum stretching (as shown in FIG. 5) and the maximum wrapping (full clockwise tip rotation, surgeon's view).

A fine 26 gauge stranded teflon-insulated wire is employed. This wire is trimmed to 3¾ inches in length and is wound on the tubular member 32 such that the total number of turns ranges between 3 and 4 as the tip is rotated through its full rotational range. In this manner, it has been found that sufficient slack remains upon full extension/rotation while, importantly, not creating undue excess wire when the handpiece is operated at its diametric extreme, i.e. maximum compression and unwrapping of the wire.

It will be appreciated that the orientation of the tubular member 32 with respect to the housing should remain as set (unless reset) by the surgeon for the particular operative procedure contemplated. To this end, the previously mentioned locking collet 38 serves doubleduty. As mentioned, collet 38 functions first to permit the axial and annular movement of guide tube 36 therethrough. For locking, however, this collet is compressed to form a tight locking grip around the inner guide tube 36 thereby precluding all movement thereof, both axial and rotational.

More specifically, and referring to FIGS. 3 and 4, a slot 54 extends longitudinally along the entire length of collet 38. Further, the proximal end of the collet is formed as a tapered conical section which, in turn, is engaged by the forward edge of the rear housing 30 as this latter member is threadably received into the main housing 24. Thus, the rear housing 30 is urged against the sloped collet surface thereby causing the collet to compress around the guide tube 36 locking, as noted, this tube against movement.

Referring again to FIG. 1, the isolation interface 14 for the present touch-control handpiece incorporates a self-contained lithium battery and opto-isolator (not shown), the output of which is connected to electrical plug 60. The battery, touch-control switch 34 and opto-isolator are interconnected such that an output single is present at plug 60 whenever switch 34 is depressed. It will be appreciated that through the use of an extremely low voltage internal battery source (i.e. approximately 1 volt) and the opto-isolator, the patient is protected against any possibility of inadvertent electrical shock.

We claim:

1. An adjustable handpiece for use in laser surgery including a housing for physically grasping the handpiece during the surgical use thereof; a generally elongated member extending from the housing and having a proximal end an a distal end, the distal end of the elongated member defining a laser energy output for performing surgical operations on human tissue; an optical fiber having a first proximal end for connection to a laser source and a second distal end, the optical fiber extending through the housing and elongated member and means for securing the fiber to the elongate member whereby the distal end of the fiber generally coincides with the distal end of the elongate member; switch means on the housing for enabling operation of the laser source; means for adjustably fixing the elongate member to the housing and for permitting axial and rotational adjustment of the relative orientation of the elongate member with respect to the housing using mechanical means within the housing that moves the elongated member, whereby the distal end of the elongate member may be oriented as desired by a surgeon with respect to the housing and switch means thereon.

2. The adjustable handpiece of claim 1 in which the switch means for enabling the laser source operation includes a switch on the housing and means for operatively interconnecting the switch with the laser source whereby actuation of the switch causes the corresponding enablement of the laser source.

3. The adjustable handpiece of claim 2 in which the means for operatively interconnecting the switch and the laser source includes an optical transmitter and a low voltage battery for powering said transmitting, the battery and transmitter being operatively connected to the switch whereby the transmitter outputs an optical signal in response to actuation of the switch; an optical receiver adjacent the transmitter for receiving the optical transmitter output signal; means for interconnecting the optical receiver to the laser source whereby the laser source is selectably enabled by the actuation of the switch on the handpiece housing through said optical interconnections between the handpiece and laser source whereby any possibility of inadvertent electrical shock to the patient or attending surgeon caused by the handpiece is eliminated.

4. The adjustable handpiece of claim 2 in which the means for operatively interconnecting the switch with the laser source includes wires, said wires being connected to the switch and being positioned within the housing adjacent the optical fiber and extending generally therealong to the proximal end of said fiber; and means for protecting the wires whereby the elongate member may be oriented without damage to the wires.

5. The adjustable handpiece of claim 4 in which the means for protecting the wires includes means for restricting the axial travel of the elongate member between first retracted and second extended positions and means for restricting the rotational movement of the elongate member between first and second rotational limit positions.

6. The adjustable handpiece of claim 5 in which the means for restricting the rotational movement of the elongate member includes a longitudinal ridge rigidly affixed to the housing and an abutment member extending radially outwardly from the elongate member, said abutment member being in proximity to the longitudinal ridge whereby an interference between the abutment member and ridge limits the rotational movement of the elongate member while simultaneously permitting axial travel thereof.

7. The adjustable handpiece of claim 4 in which the wires are formed into a helix having a predetermined number of turns around the elongate member whereby the axial travel of the elongate member correspondingly stretches and compresses the axial length of the helix and whereby the rotational movement of the elongate member correspondingly tightens and loosens the helix whereby the elongate member may be oriented through its full range of axial and rotational movements without overstressing or tangling the wires.

8. An adjustable handpiece for use in laser surgery including a housing for physically grasping the handpiece during the surgical use thereof; a generally elongate member extending from the housing and having a proximal end and a distal end, the distal end of the elongate member defining a laser energy output for performing surgical operations on human tissue; an optical fiber having a first proximal end for connection to a laser source and a second distal end, the optical fiber extending through the housing and elongate member and means for securing the fiber to the elongate member whereby the distal end of the fiber generally coincides with the distal end of the elongate member; a switch on the housing and an optical transmitter; a low voltage battery for powering said transmitter, the battery and transmitter being operatively connected to the switch whereby the transmitter outputs an optical signal in response to actuation of the switch, an optical receiver adjacent the transmitter for receiving the optical transmitter output signal; means for interconnecting the optical receiver to the laser source whereby the laser source is selectably enabled by the actuation of the switch on the handpiece housing through said optical interconnection between the handpiece and the laser source whereby any possibility of inadvertent electrical shock to the patient or attending surgeon caused by the handpiece is eliminated; and means for adjustably fixing the elongate member to the housing and for permitting adjustment of the relative orientation of the elongate member with respect to the housing using mechanical means within the housing, whereby the distal end of the elongate member may be oriented as desired by a surgeon with respect to the housing and switch means thereon.

9. An adjustable handpiece for use in laser surgery including a housing for physically grasping the handpiece during the surgical use thereof; a generally elongate member extending from the housing and having a proximal end and a distal end, the distal end of the elongate member defining a laser energy output for performing surgical operations on human tissue; an optical fiber having a first proximal end for connection to a laser source and a second distal end, the optical fiber extending through the housing and elongate member and means for securing the fiber to the elongate member whereby the distal end of the fiber generally coincides with the distal end of the elongate member; a switch on the housing and wires operatively interconnecting the switch with the laser source whereby actuation of the switch causes the corresponding enablement of the laser source, said wires being connected to the switch and being positioned within the housing adjacent the optical fiber and extending generally therealong to the proximal end of said fiber; means for protecting the wires whereby the elongate member may be oriented without damage to the wires; and means for restricting the axial travel of the elongate member between first retracted and second extended positions and means for restricting the rotational movement of the elongate member between first and second rotational limit positions.

10. The adjustable handpiece of claim 9, in which the means for restricting the rotational movement of the elongate member includes a longitudinal ridge rigidly affixed to the housing and an abutment member extending radially outwardly from the elongate member, said abutment member being in proximity to the longitudinal ridge whereby an interference between the abutment member and ridge limits the rotational movement of the elongate member while simultaneously permitting axial travel thereof.

11. The adjustable handpiece of claim 9, in which the wires are formed into a helix having a predetermined number of turns around the elongate member, whereby the axial travel of the elongate member correspondingly stretches and compresses the axial length of the helix and whereby the rotational movement of the elongate member correspondingly tightens and loosens the helix, whereby the elongate member may be oriented through a full range of axial and rotational movements without overstressing or tangling the wires.

12. An adjustable handpiece for use in laser surgery including a housing for physically grasping the handpiece during the surgical use thereof; a generally elongate member extending from the housing and having a proximal end and a distal end, the distal end of the elongate member defining a laser energy output for performing surgical operations on human tissue; an optical fiber having a first proximal end for connection to a laser source and a second distal end, the optical fiber extending through the housing and elongate member and means for securing the fiber to the elongate member whereby the distal end of the fiber generally coincides with the distal end of the elongate member; switch means on the housing for enabling operation of the laser source; means for adjustably fixing the elongate member to the housing and for permitting axial adjustment of the relative orientation of the elongate member with respect to the housing into a plurality of working positions by using mechanical means within the housing, whereby the distal end of the elongate member may be oriented as desired by a surgeon with respect to the housing and switch means thereon.

13. The adjustable handpiece of claim 12 in which the switch means for enabling the laser source operation includes a switch on the housing and means for operatively interconnecting the switch with the laser source whereby actuation of the switch causes the corresponding enablement of the laser source.

14. The adjustable handpiece of claim 13 in which the means for operatively interconnecting the switch and the laser source includes an optical transmitter and a low voltage battery for powering said transmitting, the battery and transmitter being operatively connected to the switch whereby the transmitter outputs an optical signal in response to actuation of the switch; an optical receiver adjacent the transmitter for receiving the optical transmitter output signal; means for interconnecting the optical receiver to the laser source whereby the laser source is selectably enabled by the actuation of the switch on the handpiece housing through said optical interconnections between the handpiece and laser source whereby any possibility of inadvertent electrical shock to the patient or attending surgeon caused by the handpiece is eliminated.

15. The adjustable handpiece of claim 13 in which the means for operatively interconnecting the switch with the laser source includes wires, said wires being connected to the switch and being positioned within the housing adjacent the optical fiber and extending generally therealong to the proximal end of said fiber; and means for protecting the wires whereby the elongate member may be oriented without damage to the wires.

16. The adjustable handpiece of claim 15 in which the means for protecting the wires includes means for restricting the axial travel of the elongate member between first retracted and second extended positions.

17. The adjustable handpiece of handpiece of claim 16 in which the wires are formed into a helix having a predetermined number of turns around the elongate member whereby the axial travel of the elongate member correspondingly stretches and compresses the axial length of the helix, and whereby the elongate member may be oriented through its full range of axial movements without overstressing or tangling the wires.

* * * * *

UNITED STATES PATENT AND TRADEMARK OFFICE
CERTIFICATE OF CORRECTION

PATENT NO. : 5,221,279
DATED : June 22, 1993
INVENTOR(S) : Cook, et al

It is certified that error appears in the above-indentified patent and that said Letters Patent is hereby corrected as shown below:

Column 4, line 8: insert --tubular-- after "rotate the."

Column 4, line 30: delete "to be."

Column 4, line 34: change "housing" to --bushing--.

Column 4, line 46: change "fluid/conduit" to --fluid/gas conduit--.

Column 4, line 63: change "of" (first occurrence) to --or--.

Column 5, line 26: change 3¾ to --3 ⅛--.

Column 5, line 40: insert --as bushing-- after "first."

Column 5, line 41: change "annular" to --angular--.

Column 5, line 62: change "single" to --signal--.

Column 6, lines 3-4: change "elongated" to --elongate--.

Column 6, line 5: change "an" to --and--.

Column 6, lines 5-6: change "elongated" to --elongate --.

Column 6, line 10: change "elongated" to --elongate--.

UNITED STATES PATENT AND TRADEMARK OFFICE
CERTIFICATE OF CORRECTION

PATENT NO. : 5,221,279
DATED : June 22, 1993
INVENTOR(S) : Cook et al

It is certified that error appears in the above-indentified patent and that said Letters Patent is hereby corrected as shown below:

Column 6, lines 17-18: change "elongated" to --elongate--.

Column 8, line 46: insert --that moves the elongate member-- after "housing" and before the comma.

Column 10, line 3: delete --handpiece of-- (second occurrence).

Column 10, line 4: change "16" to --15--.

Signed and Sealed this

Eighth Day of March, 1994

*Attest:*

BRUCE LEHMAN

*Attesting Officer*     Commissioner of Patents and Trademarks